(12) United States Patent
Park et al.

(10) Patent No.: US 10,653,363 B2
(45) Date of Patent: May 19, 2020

(54) TOPOLOGICAL EVOLUTION OF TUMOR IMAGERY

(71) Applicant: INTERNATIONAL BUSINESS MACHINES CORPORATION, Armonk, NY (US)

(72) Inventors: Sun Young Park, San Diego, CA (US); Dustin Sargent, San Diego, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/554,902

(22) Filed: Aug. 29, 2019

(65) Prior Publication Data

US 2019/0380656 A1 Dec. 19, 2019

Related U.S. Application Data

(63) Continuation of application No. 15/421,023, filed on Jan. 31, 2017.

(51) Int. Cl.
| | | |
|---|---|---|
| *G06K 9/00* | (2006.01) | |
| *A61B 5/00* | (2006.01) | |
| *A61B 5/055* | (2006.01) | |
| *A61B 6/03* | (2006.01) | |
| *A61B 6/00* | (2006.01) | |
| *A61B 8/08* | (2006.01) | |
| *A61B 90/00* | (2016.01) | |

(Continued)

(52) U.S. Cl.
CPC ............ *A61B 5/7264* (2013.01); *A61B 5/055* (2013.01); *A61B 5/4842* (2013.01); *A61B 6/032* (2013.01); *A61B 6/486* (2013.01); *A61B 6/5217* (2013.01); *A61B 6/5247* (2013.01); *A61B 8/085* (2013.01); *A61B 8/5223* (2013.01); *A61B 8/5261* (2013.01); *A61B 90/37* (2016.02); *G06K 9/00* (2013.01); *G06K 9/342* (2013.01); *G06T 7/0016* (2013.01); *G06T 7/30* (2017.01); *G16H 30/20* (2018.01); *G16H 30/40* (2018.01); *G16H 50/20* (2018.01); *A61B 5/004* (2013.01); *A61B 5/7275* (2013.01); *A61B 2090/364* (2016.02); *A61B 2576/02* (2013.01); *A61B 2576/026* (2013.01); *G06K 9/6277* (2013.01); *G06K 2209/05* (2013.01); *G06T 2207/20084* (2013.01); *G06T 2207/30016* (2013.01); *G06T 2207/30096* (2013.01)

(58) Field of Classification Search
None
See application file for complete search history.

(56) References Cited

U.S. PATENT DOCUMENTS 7,072,501 B2 7/2006 Wood et al.
7,149,564 B2 12/2006 Vining et al.
(Continued)

*Primary Examiner* — Atiba O Fitzpatrick
(74) *Attorney, Agent, or Firm* — Erik Huestis; Stephen Kenny; Foley Hoag, LLP

(57) ABSTRACT

Topological evolution of a lesion within a time series of medical imagery is provided. In various embodiments, a time series of medical images is read. Each of the images depicts a subject anatomy and a lesion. The lesion has a size and a contour within each of the medical images. At least one anatomical label is read for the subject anatomy within each of the plurality of images. Based upon the contour of the lesion within each of the medical images and based on the at least one anatomical label, a further contour of the lesion is predicted outside of the time series.

20 Claims, 10 Drawing Sheets

(51) Int. Cl.

| | | |
|---|---|---|
| *G06T 7/00* | (2017.01) | |
| *G06T 7/30* | (2017.01) | |
| *G06K 9/34* | (2006.01) | |
| *G16H 50/20* | (2018.01) | |
| *G16H 30/40* | (2018.01) | |
| *G16H 30/20* | (2018.01) | |
| *G06K 9/62* | (2006.01) | |

(56) References Cited

U.S. PATENT DOCUMENTS

| | | |
|---|---|---|
| 7,503,559 B2 | 3/2009 | Yoshida |
| 8,155,405 B2 | 4/2012 | Unal et al. |
| 8,611,622 B2 | 12/2013 | Vincent et al. |
| 9,277,902 B2 | 3/2016 | Mullick et al. |
| 9,706,935 B2 | 7/2017 | Spector |
| 2003/0174872 A1 | 9/2003 | Chalana et al. |
| 2011/0268336 A1 | 11/2011 | Dmitrieva et al. |
| 2014/0011173 A1 | 1/2014 | Tepper et al. |
| 2015/0005630 A1 | 1/2015 | Jung et al. |
| 2016/0015364 A1 | 1/2016 | Kurita et al. |
| 2016/0048965 A1 | 2/2016 | Stehle et al. |

TOPOLOGICAL EVOLUTION OF TUMOR IMAGERY

CROSS-REFERENCE TO RELATED APPLICATIONS

This application is a continuation of U.S. patent application Ser. No. 15/421,023, filed on Jan. 31, 2017, which is hereby incorporated by reference in its entirety.

BACKGROUND

Embodiments of the present invention relate to medical imagery, and more specifically, to topological evolution of a lesion within a time series of medical imagery.

BRIEF SUMMARY

According to various embodiments of the present disclosure, methods of and computer program products for topological evolution of a lesion are provided. A time series of medical images is read. Each of the images depicts a subject anatomy and a lesion. The lesion has a size and a contour within each of the medical images. At least one anatomical label is read for the subject anatomy within each of the plurality of images. Based upon the contour of the lesion within each of the medical images and based on the at least one anatomical label, a further contour of the lesion is predicted outside of the time series.

DETAILED DESCRIPTION

Figure 1:
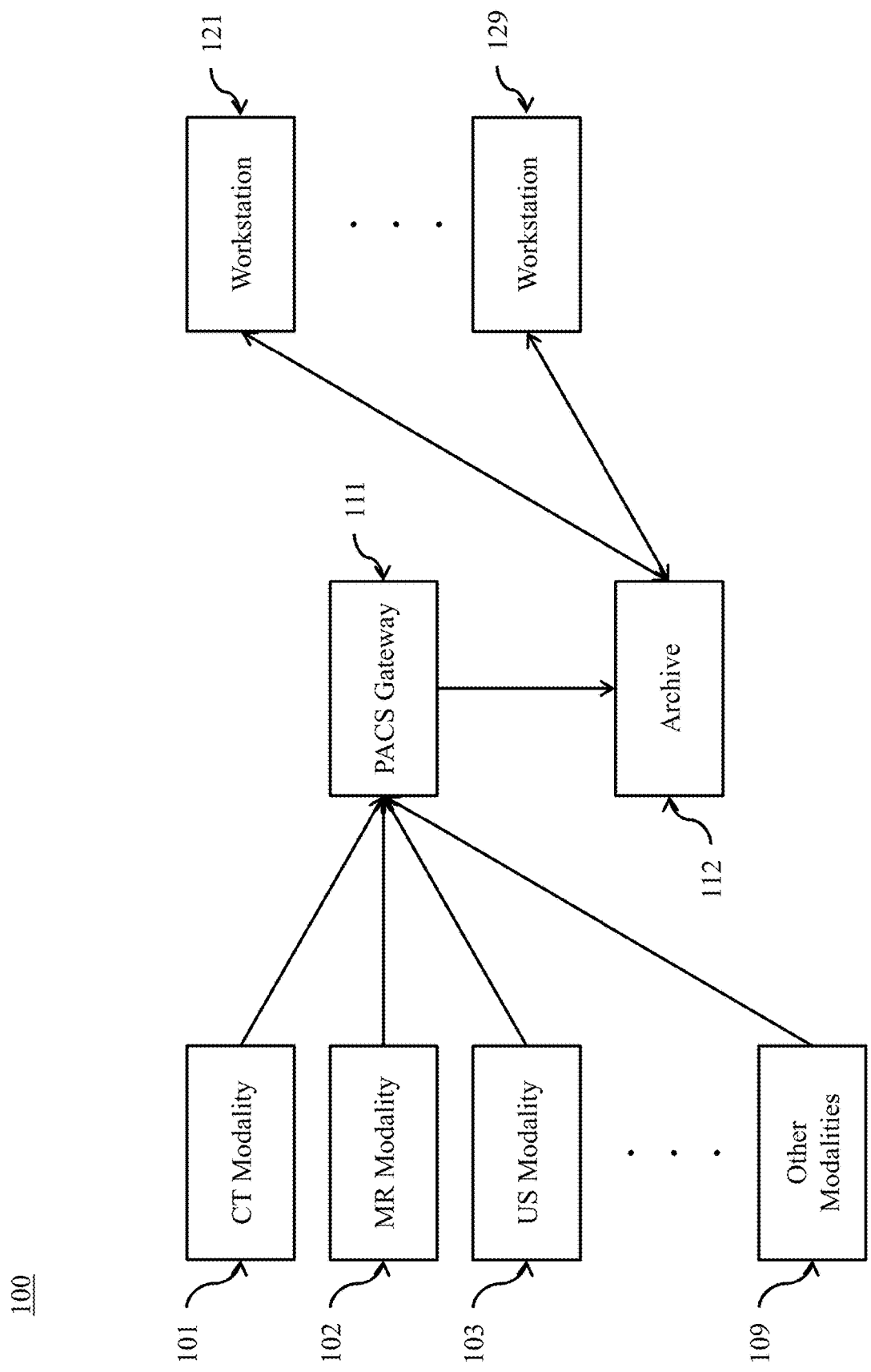
FIG. 1 depicts an exemplary Picture Archiving and Communication System.

Tumor tracking and progression analysis using medical images is a crucial task for physicians to provide accurate and efficient treatment plans. The present disclosure provides a generalized tumor propagation model considering time-series prior images and local anatomical features. In some embodiments, a hierarchical Hidden Markov Model is used for tumor tracking. In other embodiments, a dynamic Bayesian network (DBN), conditional random field (CRF), a support vector machine (SVM), or an recurrent neural network (RNN) is used. It will be appreciated that a variety of learning systems and algorithms suitable for time series data may be applied for tumor tracking according to the present disclosure. The propagation model describes the lesion propagation between prior and current images, and between adjacent images within the same series. The anatomical tissue structure of the targeted body part is extracted and the local tissue properties are incorporated in the model. The model identifies a diagnostic relationship between different tissue types, their locations and neighboring regions.

The Tumor tracking models according to embodiments of the present disclosure are suitable for integration into various clinical systems. For example, topological evolution of contour imagery according to embodiments of the present disclosure may be used together with manual annotations or an automated CAD system. The teachings of the present disclosure can support the manual annotation process, leading to speed and accuracy increases. Similarly, the teachings of the present disclosure can compensate for the risk of inaccurate outcomes from CAD systems.

The methods set out herein are suitable for application to diverse tumor exams including brain tumors, lung nodules and liver cancer exams with priors. The present disclosure is applicable to general tumor propagation problems for practical use in a tumor tracking application.

A Picture Archiving and Communication System (PACS) is a medical imaging system that provides storage and access to images from multiple modalities. In many heathcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

The present disclosure provides a generalized lesion propagation model to improve tumor and other feature tracking and predication analysis in medical images. The model incorporates time-series lesion information and local neighboring tissue information. Various embodiments take advantage of the observation that the probability of tumor detection in a given exam is conditionally dependent upon the presence of tumors in prior exams, and that the local tissue type surrounding the tumor has a spatial relationship with the tumor's local growth or reduction in size. The model may be incorporated together with user-guided tumor segmentation in an oncology viewer application according to various embodiments of the present disclosure.

Hand annotation is error prone and time consuming. Simple edge detection does not take into account the progression of a mass over time. To address this problem, the present disclosure provides for evolution of identified masses as an aid to annotation.

According to various embodiments of the present disclosure, a mass is initially hand annotated. Treatment information is input to the system, and additional imagery is hand annotated. The hand annotated contours are used to train an image analysis system. Once trained, the image analysis system is used to evolve a new contour. The new contour is overlain on subsequently gathered imagery as a suggested contour. A user then has the ability to adjust or accept the contour.

By deriving a projected new contour on the basis of treatment information, the user need not hand annotate from scratch, thereby reducing errors. This is less computationally intensive than performing new feature extraction.

In various embodiments, multiple tumor volumes (or contours) are generated with an evolutional learning process using other tumor images. Other tumor images may include tumor evolution features from the current exam's priors or other patient's exams. The prior exam images are aligned to the current exam images utilizing neighboring anatomical features around the lesion. The evolutional learning process includes tumor growth, shrinking, splitting into multiple tumors. Evolution learning process uses the following tumor characteristics including growing or shrinking near the area of prior tumor and tumor spreading speed could be different based on neighboring tissue characteristics.

In various embodiments, a user may select the target tumor with different scores or colors. The generated multiple tumor volumes may have assigned probabilities based on the relevance of similarity with the existing priors. This may be translated into scores or colors. The relevancy of similarity includes the intensity, texture, tumor shape, neighbor tissue, or speed of tumor growth/shrink.

Referring to FIG. 1, an exemplary PACS 100 consists of four major components. Various imaging modalities 101 . . . 109 such as computed tomography (CT) 101, magnetic resonance imaging (MM) 102, or ultrasound (US) 103 provide imagery to the system. In some implementations, imagery is transmitted to a PACS Gateway 111, before being stored in archive 112. Archive 112 provides for the storage and retrieval of images and reports. Workstations 121 . . . 129 provide for interpreting and reviewing images in archive 112. In some embodiments, a secured network is used for the transmission of patient information between the components of the system. In some embodiments, workstations 121 . . . 129 may be web-based viewers. PACS delivers timely and efficient access to images, interpretations, and related data, eliminating the drawbacks of traditional film-based image retrieval, distribution, and display.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Different users may have a different view into the overall PACS system. For example, while a radiologist may typically access a viewing station, a technologist may typically access a QA workstation.

In some implementations, the PACS Gateway 111 comprises a quality assurance (QA) workstation. The QA workstation provides a checkpoint to make sure patient demographics are correct as well as other important attributes of a study. If the study information is correct the images are passed to the archive 112 for storage. The central storage device, archive 112, stores images and in some implementations, reports, measurements and other information that resides with the images.

Once images are stored to archive 112, they may be accessed from reading workstations 121 . . . 129. The reading workstation is where a radiologist reviews the patient's study and formulates their diagnosis. In some implementations, a reporting package is tied to the reading workstation to assist the radiologist with dictating a final report. A variety of reporting systems may be integrated with the PACS, including those that rely upon traditional dictation. In some implementations, CD or DVD authoring software is included in workstations 121 . . . 129 to burn patient studies for distribution to patients or referring physicians.

In some implementations, a PACS includes web-based interfaces for workstations 121 . . . 129. Such web interfaces may be accessed via the internet or a Wide Area Network (WAN). In some implementations, connection security is provided by a VPN (Virtual Private Network) or SSL (Secure Sockets Layer). The clients side software may comprise ActiveX, JavaScript, or a Java Applet. PACS clients may also be full applications which utilize the full resources of the computer they are executing on outside of the web environment.

Communication within PACS is generally provided via Digital Imaging and Communications in Medicine (DICOM). DICOM provides a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format.

DICOM groups information into data sets. For example, a file containing a particular image, generally contains a patient ID within the file, so that the image can never be separated from this information by mistake. A DICOM data object consists of a number of attributes, including items such as name and patient ID, as well as a special attribute containing the image pixel data. Thus, the main object has no header as such, but instead comprises a list of attributes, including the pixel data. A DICOM object containing pixel data may correspond to a single image, or may contain multiple frames, allowing storage of cine loops or other multi-frame data. DICOM supports three- or four-dimensional data encapsulated in a single DICOM object. Pixel data may be compressed using a variety of standards, including JPEG, Lossless JPEG, JPEG 2000, and Run-length encoding (RLE). LZW (zip) compression may be used for the whole data set or just the pixel data.

Figure 2:
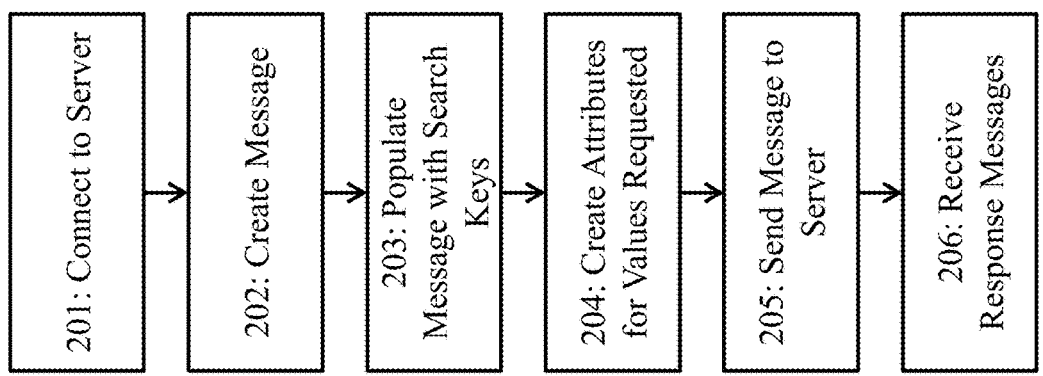
FIG. 2 illustrates an exemplary clinical image search and retrieval method.

Referring to FIG. 2, an exemplary PACS image search and retrieval method 200 is depicted. Communication with a PACS server, such as archive 112, is done through DICOM messages that that contain attributes tailored to each request. At 201, a client, such as workstation 121, establishes a network connection to a PACS server. At 202, the client prepares a DICOM message, which may be a C-FIND, C-MOVE, C-GET, or C-STORE request. At 203, the client fills in the DICOM message with the keys that should be matched. For example, to search by patient ID, a patient ID attribute is included. At 204, the client creates empty attributes for all the values that are being requested from the server. For example, if the client is requesting an image ID suitable for future retrieval of an image, it include an empty attribute for an image ID in the message. At 205, the client send the message to the server. At 206, the server sends back to the client a list of one or more response messages, each of which includes a list of DICOM attributes, populated with values for each match.

Figure 3:
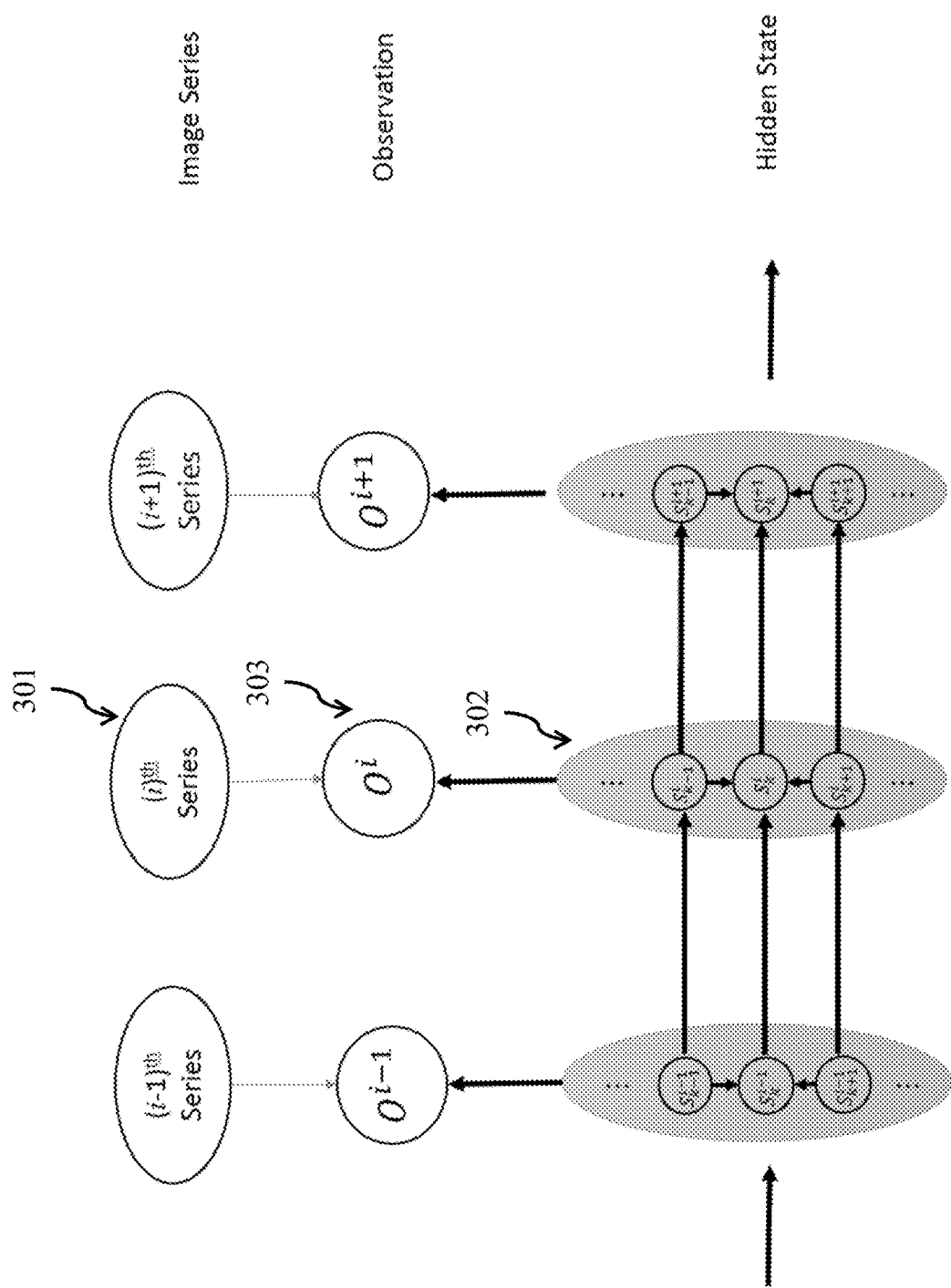
FIG. 3 illustrates a tumor propagation model according to embodiments of the present disclosure.

Referring to FIG. 3, a tumor propagation model according to embodiments of the present disclosure is illustrated. A generalized Hidden Markov Model is applied for each tissue type to model the relationships between prior lesions in the same tissue type as well as the relationships of the current predicted lesions between the neighboring tissue types to identify the tumors in an image series.

Given an image series 301 with I images, let $f^i$ denote the $i^{th}$ image in the series; then, image series $f^i$ is composed of K disjoint tissue regions $r_k^i$, k=1, ..., K. The neighborhood $\partial_{j,k}^i$ of tissue region $r_k^i$ is defined as the set of tissue regions adjacent to region $r_k^i$. Following the stochastic HMM framework, a hidden state $s_k^i$ is defined, representing whether or not the lesion is contained in tissue region $r_k^i$. An observation $o_k^i$ is defined by the part of the images corresponding to tissue region $r_k^i$. Finally, random variables $S_k^i$ 302 and $O_k^i$ 303 are defined to represent state $s_k^i$ and observation $o_k^i$. Then, by the Markov property, the joint conditional probability density function p(s|O=o) follows a Gibbs distribution, and is written according to Equation 1, where s={$s_k^i$|i=1, ..., I and k=1, ..., K}, O={$O_k^i$|i=1, ..., I and k=1, ... K}, o={$o_k^i$|i=1, ..., I and k=1, ... K}, $N_k^i$ denotes the set of states of the neighbor tissues of $s_k^i$ such that $N_k^i$={$s_l^i$|$r_l \in \partial_k^i$, l=1, ..., K}, t is a transition feature function, u is a state feature function, λ and μ are parameters to be estimated, and Z(o) is a normalization factor according to Equation 2.

$$p(s|O=o) = \frac{1}{Z(o)} \exp\left(\sum_{i=1}^{i=I}\left(\sum_{k=1,\sigma^i \in N_k^i}^{k=K} \lambda \cdot t(\sigma^i, s_k^{i-1}, s_k^i, o_k^i) + \sum_{k=1}^{K} \mu \cdot u(s_k^i, o_k^i)\right)\right) \quad \text{Equation 1}$$

$$Z(o) = \sum_s \exp\left(\sum_{i=1}^{i=I}\left(\sum_{k=1,\sigma^i \in N_k^i}^{k=K} \lambda \cdot t(\sigma^i, s_k^{i-1}, s_k^i, o_k^i) + \sum_{k=1}^{K} \mu \cdot u(s_k^i, o_k^i)\right)\right) \quad \text{Equation 2}$$

Figure 4:
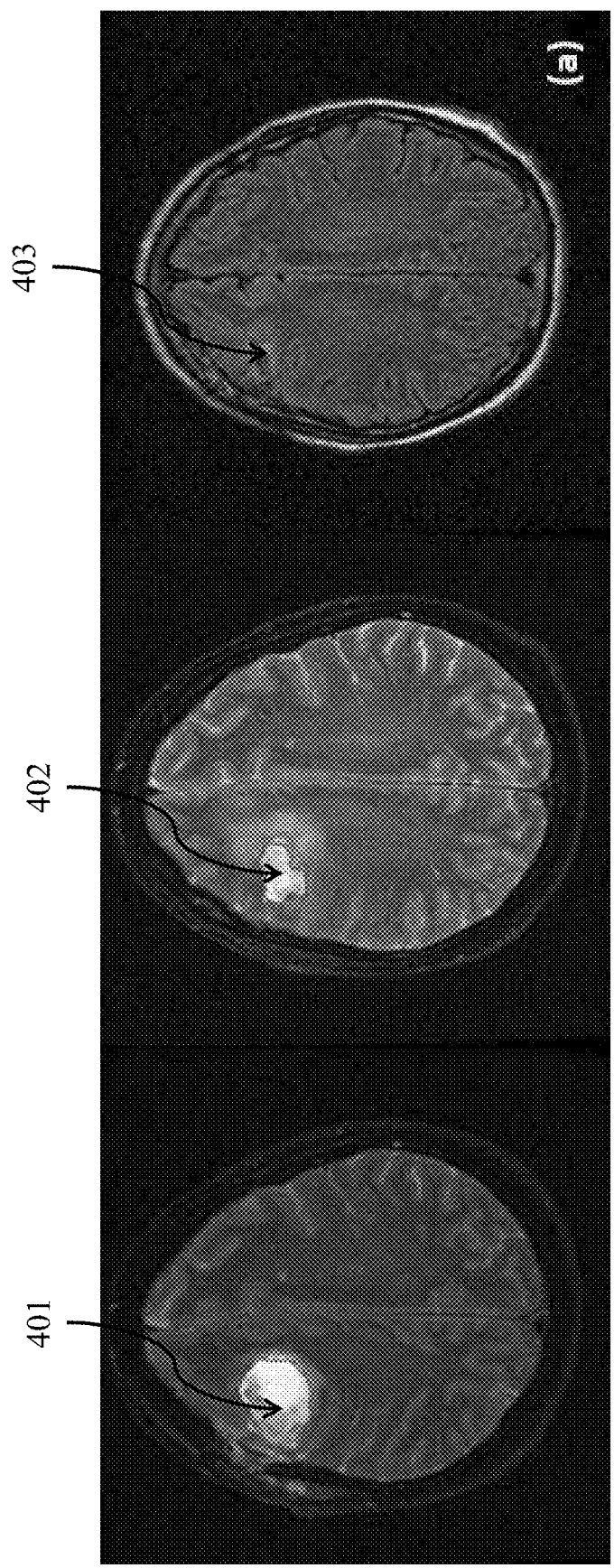
FIG. 4 illustrates exemplary propagation of a tumor in brain MM according to embodiments of the present disclosure.
Figure 5:
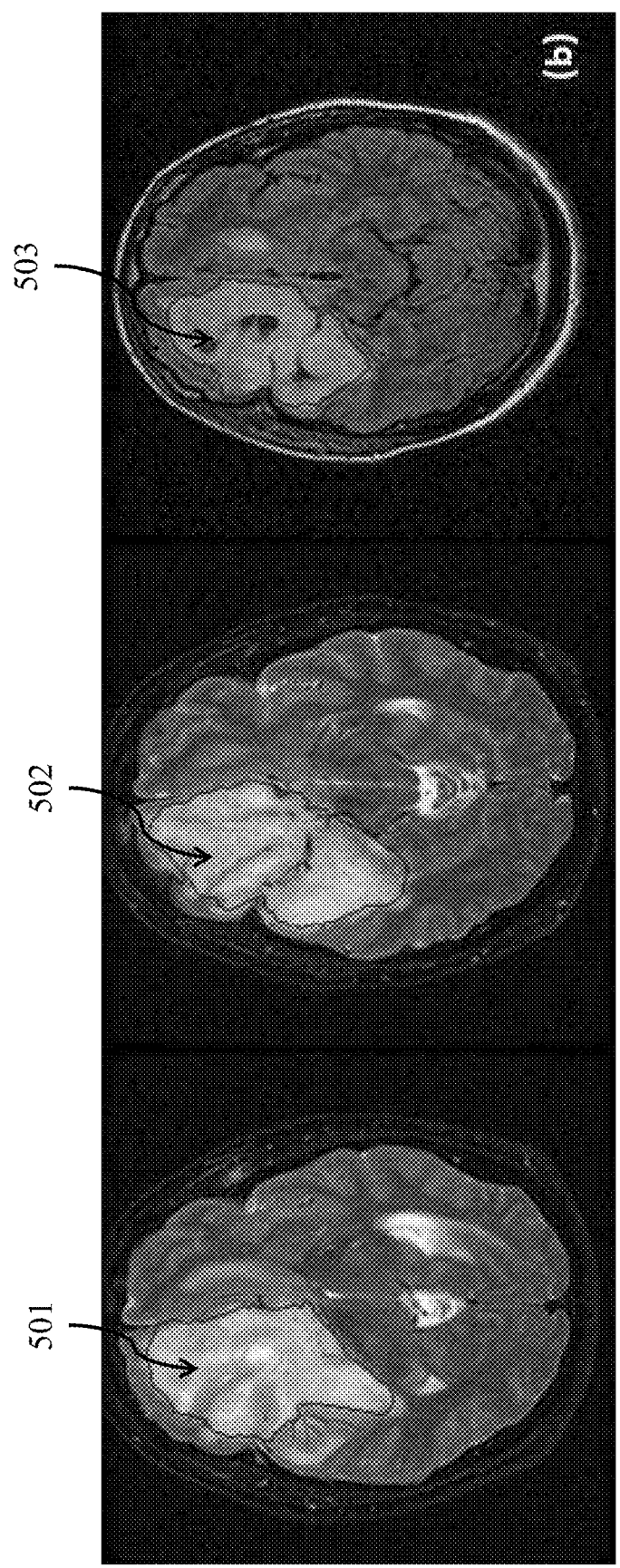
FIG. 5 illustrates exemplary propagation of an edema in brain MM according to embodiments of the present disclosure.

Referring to FIGS. 4-5, exemplary propagation of a tumor and an edema are illustrated. Each figure depicts an exemplary MRI brain image. Each figure shows results of tumor and edema propagation between prior and current brain exams. The three brain MR exams in each sequence were acquired within a 10 month span. In FIG. 4, predicted outlines of a tumor are depicted at three points in time 401 ... 403. In FIG. 5, predicted outlines of an edema are depicted at three points in time 501 ... 503.

Figure 6:
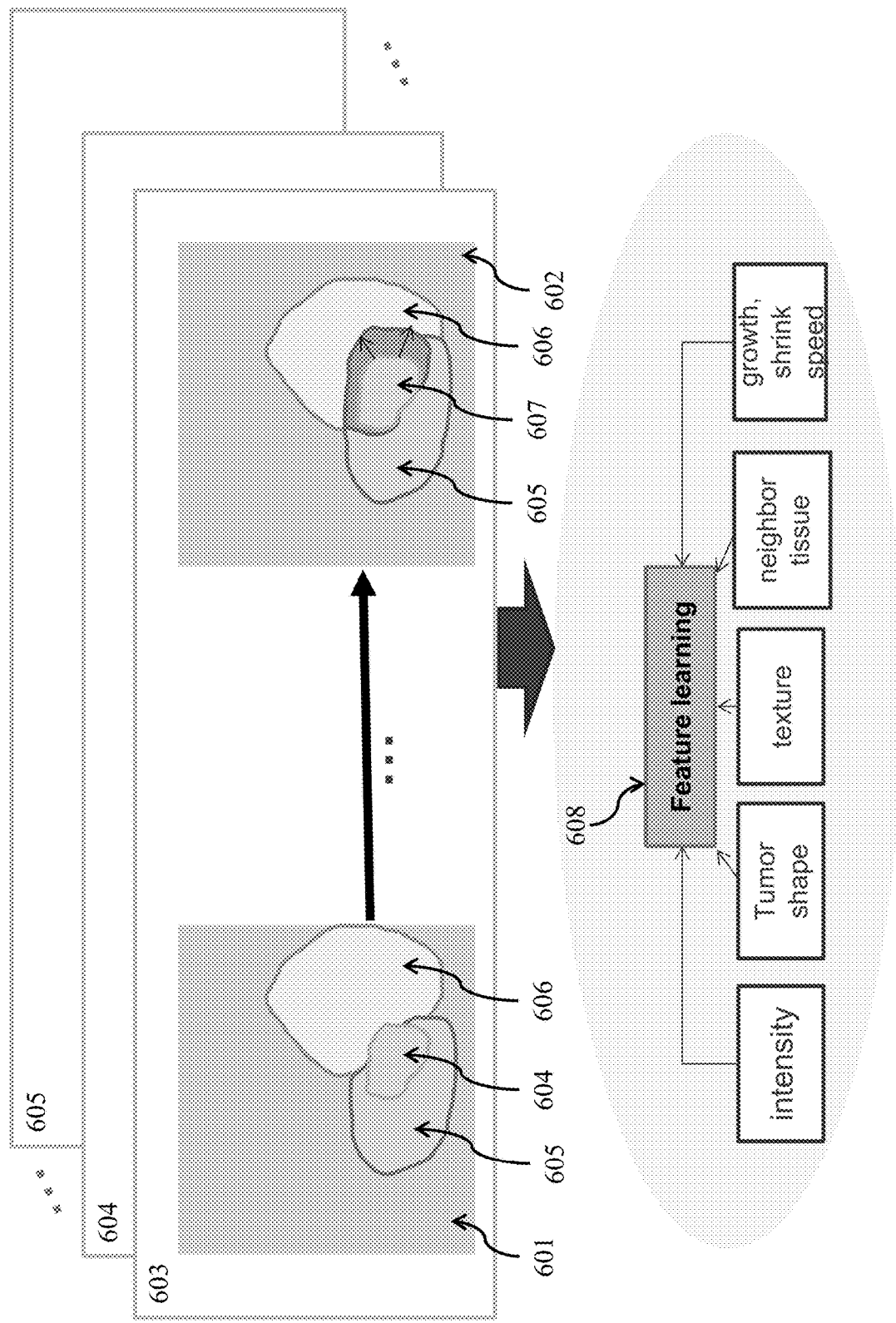
FIG. 6 illustrates a system for generation of candidate lesions through lesion progression according to embodiments of the present disclosure.

Referring to FIG. 6, a system for generation of candidate lesions through lesion progression (e.g., growth, shrink, split) is illustrated according to embodiments of the present disclosure. A plurality of prior study images 601 ... 602 associated with a patient record 603 are aligned according to the neighboring anatomic features. In various embodiments, registration is performed to align images. In exemplary image 601, lesion 604 has neighboring tissue features 605 ... 606. These features may be used to align images 601 ... 602 irrespective of the evolution of lesion 604. In exemplary image 602, lesion 604 has expanded into lesion 607. In various embodiments, multiple patient records 603 ... 605 may be analyzed as set forth above.

Prior images 601 ... 602 are used to train a feature learner 608. In some embodiments, feature learner 608 comprises a dynamic Bayesian network (DBN) such as a hidden Markov model (HMM). In some embodiments, feature learner 608 comprises a conditional random field (CRF) or a support vector machine (SVM). In some embodiments, where the prior images are not manually labeled, various segmentation algorithms may be applied to determine feature locations prior to learning. In various embodiments, the feature learner may be provided various characteristics of a lesion including intensity, lesion shape, texture, neighboring tissue characteristics, growth or shrinkage rate. For example, in the above example, the feature learner may discern that the lesion grows faster into tissue 606 than into tissue 605.

Figure 7:
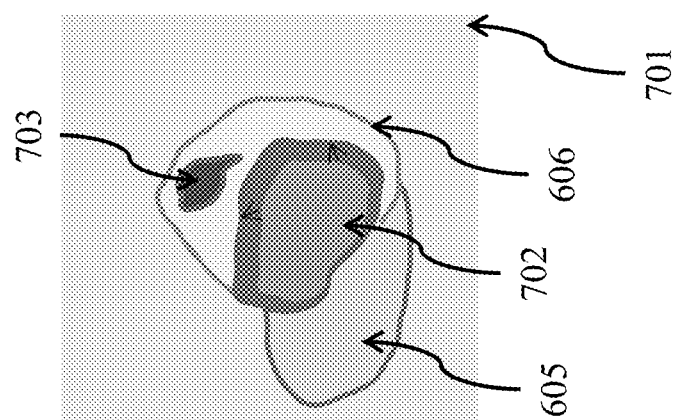
FIG. 7 illustrates exemplary candidate lesion identification according to embodiments of the present disclosure.

Referring to FIG. 7, exemplary candidate lesion identification is illustrated according to embodiments of the present disclosure. When new image 701 is collected, it is correlated to prior images 601 ... 602. Tissue features 605 and 606 are thereby located. Applying the trained learner to input image 701, a current shape of lesion 702 is predicted, as is additional candidate lesion 703. In this way, candidate lesions for examination or labeling may be generated from a time series of images for a given patient, or from a plurality of time series for more than one patient.

Figure 8:
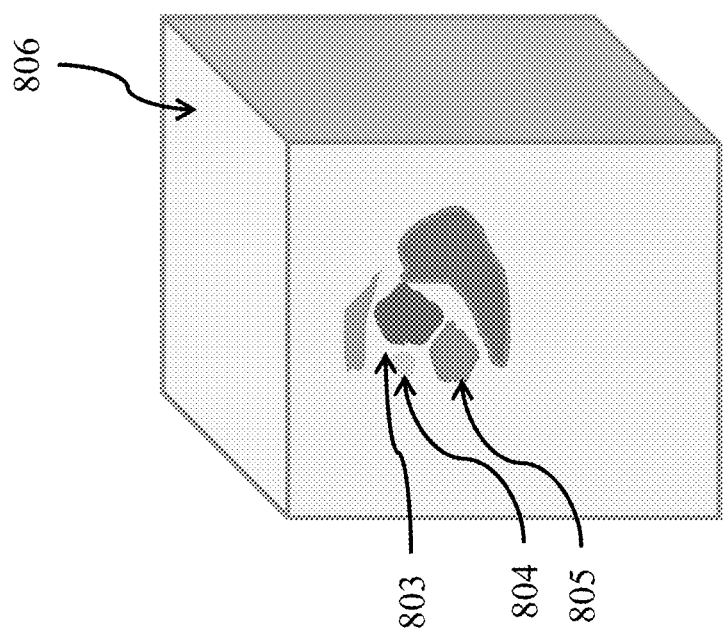
FIG. 8 illustrates exemplary multiple candidate generation according to embodiments of the present disclosure.
Figure 8:
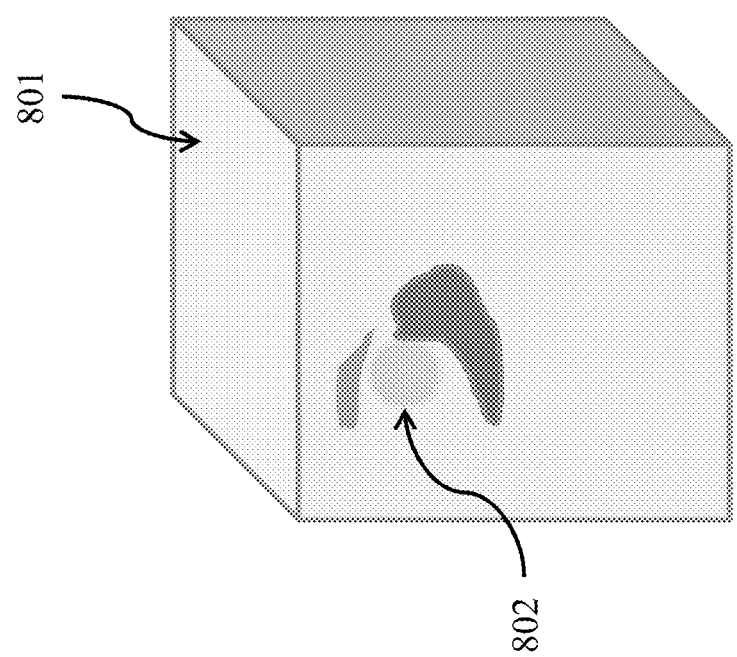

Referring to FIG. 8, exemplary multiple candidate generation is illustrated according to embodiments of the present disclosure. Prior volume 801 includes lesion 802. Based on prior image 801, candidate lesions 803 ... 805 are identified in current volume 806.

As set forth above, according to various embodiments, a tumor propagation model is provided using a generalized HMM incorporating neighboring tissue and time series lesion information. This model may be incorporated with an expert-guided or automatic lesion segmentation algorithm to propagate lesions within and between prior and current exams.

Figure 9:
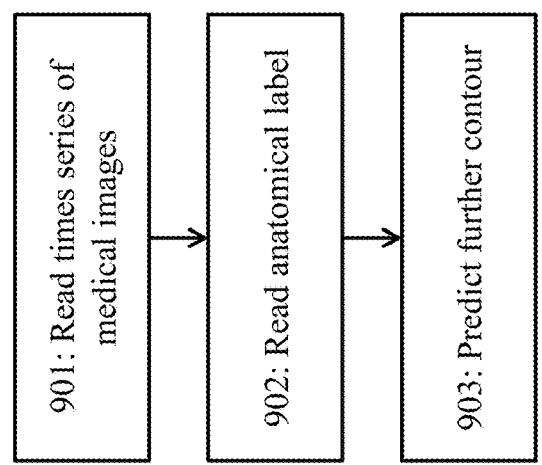
FIG. 9 illustrates a method of topological evolution of medical imagery according to embodiments of the present disclosure.

Referring to FIG. 9, a method for topological evolution of a lesion is illustrated. At 901, a time series of medical images is read. Each of the images depicts a subject anatomy and a lesion. The lesion has a size and a contour within each of the medical images. At 902, at least one anatomical label is read for the subject anatomy within each of the plurality of images. At 903, based upon the contour of the lesion within each of the medical images and based on the at least one anatomical label, a further contour of the lesion is predicted outside of the time series.

Figure 10:
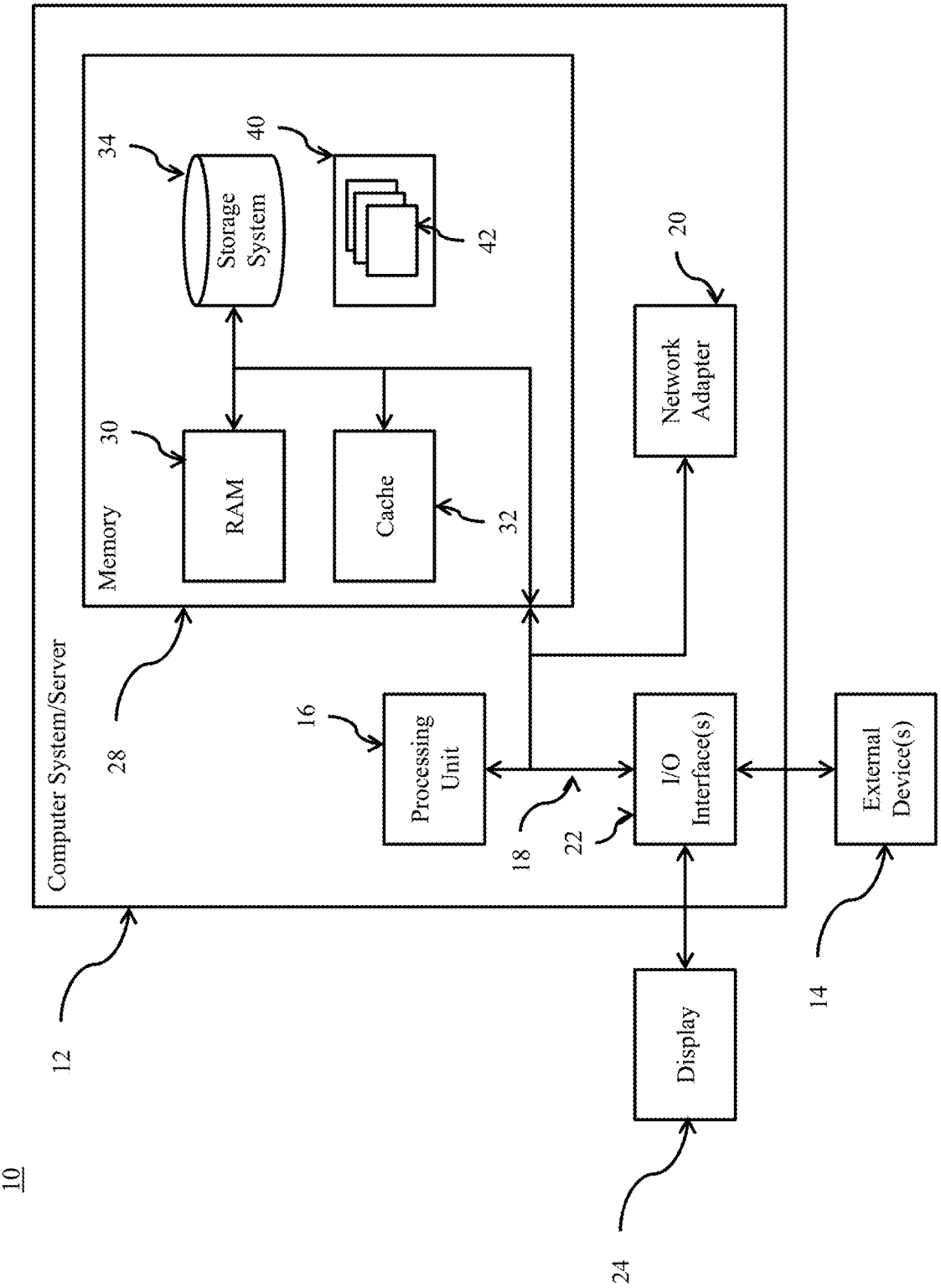
FIG. 10 depicts a computing node according to an embodiment of the present invention.

Referring now to FIG. 10, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   reading a time series of medical images, each of the images depicting a subject anatomy and a lesion, the lesion having a size and a contour within each of the medical images;
   reading at least one anatomical label for the subject anatomy within each of the plurality of images;
   dividing each of the medical images into a plurality of disjoint regions; and
   based upon the contour of the lesion within each of the medical images and based on the at least one anatomical label, predicting a further contour of the lesion outside of the time series, wherein
      predicting the further contour comprises applying a hidden Markov model to the time series of medical images, and wherein
      each of a plurality of hidden states of the hidden Markov model corresponds to whether the lesion is contained in a corresponding disjoint region of the plurality of disjoint regions.

2. The method of claim 1, wherein predicting the further contour comprises:
   determining a plurality of characteristics of the lesion over the time series.

3. The method of claim 2, wherein the plurality of characteristics comprise:
   size, shape, growth rate, shrinkage rate, intensity, texture, or neighboring tissue characteristics.

4. The method of claim 1, further comprising:
   presenting to a user the further contour overlain on a further medical image corresponding to a time later than the time series.

5. The method of claim 1, further comprising:
   aligning the medical images based on the at least one anatomical label.

6. The method of claim 5, wherein aligning the medical images comprises performing registration between the medical images.

7. The method of claim 1, further comprising:
   predicting at least one additional lesion.

8. The method of claim 1, wherein applying the hidden Markov model comprises determining whether the lesion is contained in each of the plurality of disjoint regions.

9. The method of claim 1, wherein applying the hidden Markov model comprises determining at least one tissue characteristic for each of the plurality of disjoint regions.

10. The method of claim 1, wherein applying the hidden Markov model comprises applying the hidden Markov model to each of a plurality of tissue types of the time series of medical images.

11. A system comprising:
a data store comprising a time series of medical images, each of the images depicting a subject anatomy and a lesion, the lesion having a size and a contour within each of the medical images;
a computing node comprising a computer readable storage medium having program instructions embodied therewith, the program instructions executable by a processor of the computing node to cause the processor to perform a method comprising:
reading the time series of medical images;
reading at least one anatomical label for the subject anatomy within each of the plurality of images;
dividing each of the medical images into a plurality of disjoint regions; and
based upon the contour of the lesion within each of the medical images and based on the at least one anatomical label, predicting a further contour of the lesion outside of the time series, wherein
predicting the further contour comprises applying a hidden Markov model to the time series of medical images, and wherein
each of a plurality of hidden states of the hidden Markov model corresponds to whether the lesion is contained in a corresponding disjoint region of the plurality of disjoint regions.

12. The system of claim 11, wherein predicting the further contour comprises:
determining a plurality of characteristics of the lesion over the time series.

13. The system of claim 12, wherein the plurality of characteristics comprise:
size, shape, growth rate, shrinkage rate, intensity, texture, or neighboring tissue characteristics.

14. The system of claim 11, further comprising:
a display, and wherein the method further comprises:
presenting on the display the further contour overlain on a further medical image corresponding to a time later than the time series.

15. The system of claim 11, further comprising:
aligning the medical images based on the at least one anatomical label.

16. The system of claim 15, wherein aligning the medical images comprises performing registration between the medical images.

17. The system of claim 11, wherein applying the hidden Markov model comprises determining whether the lesion is contained in each of the plurality of disjoint regions.

18. The system of claim 11, wherein applying the hidden Markov model comprises determining at least one tissue characteristic for each of the plurality of disjoint regions.

19. The system of claim 11, wherein applying the hidden Markov model comprises applying the hidden Markov model to each of a plurality of tissue types of the time series of medical images.

20. A computer program product for topological evolution of a lesion, the computer program product comprising a computer readable storage medium having program instructions embodied therewith, the program instructions executable by a processor to cause the processor to perform a method comprising:
reading a time series of medical images, each of the images depicting a subject anatomy and a lesion, the lesion having a size and a contour within each of the medical images;
reading at least one anatomical label for the subject anatomy within each of the plurality of images;
dividing each of the medical images into a plurality of disjoint regions;
based upon the contour of the lesion within each of the medical images and based on the at least one anatomical label, predicting a further contour of the lesion outside of the time series;
wherein predicting the further contour comprises applying a hidden Markov model to the time series of medical images, and
wherein each of a plurality of hidden states of the hidden Markov model corresponds to whether the lesion is contained in a corresponding disjoint region of the plurality of disjoint regions.

* * * * *